United States Patent [19]

Sedlacek et al.

[11] 4,239,743

[45] Dec. 16, 1980

[54] CARRIER-BOUND IMMUNOGLOBULIN FISSION PRODUCT AND ITS USE IN IMMUNOLOGIC ANALYSES

[75] Inventors: Hans H. Sedlacek; Friedrich R. Seiler, both of Marburg, Fed. Rep. of Germany

[73] Assignee: Behringwerke Aktiengesellschaft, Marburg, Fed. Rep. of Germany

[21] Appl. No.: 924,283

[22] Filed: Jul. 13, 1978

[30] Foreign Application Priority Data

Jul. 15, 1977 [DE] Fed. Rep. of Germany ....... 2731992
Apr. 28, 1978 [DE] Fed. Rep. of Germany ....... 2818739

[51] Int. Cl.$^2$ ...................... G01N 33/16; A61K 39/00
[52] U.S. Cl. ...................................... 424/1; 23/230 B; 435/7; 424/12; 260/112 B

[58] Field of Search ................ 195/103.5 A, 103.5 R; 424/112; 260/112 B; 23/230 B; 435/7

[56] References Cited

U.S. PATENT DOCUMENTS

| 3,966,898 | 6/1976 | Sjöquist et al. | 260/112 B |
| 4,138,213 | 2/1979 | Masson et al. | 424/1 |
| 4,143,124 | 3/1979 | Masson et al. | 424/1 |

Primary Examiner—Richard E. Schafer
Assistant Examiner—Christine M. Nucker
Attorney, Agent, or Firm—Curtis, Morris & Safford

[57] ABSTRACT

A fission product of an immunoglobulin having an immunologically functioning Fc-portion is bound to a carrier by adhesion or a chemical reaction. It can be used in an immunological analytic process for the determination of Fc-reactants in aqueous solutions.

13 Claims, No Drawings

CARRIER-BOUND IMMUNOGLOBULIN FISSION PRODUCT AND ITS USE IN IMMUNOLOGIC ANALYSES

This invention relates in the first place to a fission product of an immunoglobulin having an immunologically functioning Fc-portion, bound to a carrier by adhesion or a chemical reaction. The invention further relates to an immunological analytic process for the determination of Fc-reactants in aqueous solutions, especially in body fluids such as blood plasma or serum. More particularly, the invention relates to the determination of the Fc-reactants, rheumatoid factor and complement factors $C1_q$ and $C_3d$.

It is a further object of the present invention to provide a process for the determination of immunologically modified immunoglobulin, especially of so-called immunocomplexes, i.e. complexes formed by reaction of an antigen with an antibody. The process of the invention is used, in the first place, to determine immunocomplexes in body fluid. Because aggregates and fission products of antibodies have a behavior similar to that of immuno-complexes because of modification of the immunoglobulin, the process can also be used for the determination of said aggregates and fission products.

It is known that the determination of antibodies, antibody-antigen complexes and antigens in biological fluids, especially in body fluids such as urine or blood serum, is important to the diagnosis and therapy of various diseases, especially contagious diseases, tumor diseases, or immunological disorders. It is, therefore, desirable to have an accurate and simple process for the detection and determination of immuno-complexes.

Processes for the detection of antibody-antigen-complexes or of antibody aggregates are known. The known processes are based on the observation that the rheumatoid factor (RF) as well as the $C1_q$ component of the complex system (so-called Fc-reactants) have the property of adding on Fc-portions of immunoglobulin, which portions are bound to an antigen or to one another. Therefore, either $C1_q$ or RF has been labelled with a labelling agent, or the precipitation of antigen-antibody complexes with an appropriate test protein or the agglutination, by RF or by $C1_q$, of latex particles coated with immunoglobulin or erythrocytes coated with immunoglobulin by RF or $C1_q$ and the inhibition thereof by antigen-antibody complexes have been used for identification.

It is also known that the rheumatoid factor is represented by auto-antibodies directed against the homologous immunoglobulins. Detection is very important to the diagnosis and prognosis of rheumatic diseases.

The determination of complement factors, especially of $C1_q$ and $C_3d$, is of importance in the case of inflammatory diseases, particularly auto-immune diseases and immuno-complex diseases. A reduction in the factors results from an increased consumption thereof while an increase is due to a larger production of the factors.

It is known that the rheumatoid factors belong to the most different classes of immunoglobulins. Hitherto, detection has been carried out in agglutination processes with denatured immunoglobulins bound in the form of immuno-complexes or adsorbed onto surfaces, or by the so-called double antibody binding technique using a labelled second antibody directed against the rheumatoid factor as the first antibody [cf. Knees, Reimer, J. Immunol. Methods 18, 105–125 (1977); Hellenkofer and Mueller, Aertzl. Lab. 21, 174–181 (1975); Johnson and Faulk, Clin. Inm. Immunopathol. 6, 414–443 (1976)].

The aforesaid agglutination methods have the drawback that only rheumatoid factors of the IgM class can be detected therewith, that a differentiation between rheumatoid factors which are able to react with the $Fab_2$ part of immunoglobulins and those able to react with the Fc part is not possible, and that false positive results are obtained by serum proteins reacting with the Fc part of immunoglobulins. This is known, for example, of $C1_q$ of the complement system.

The disadvantage of the double antibody binding methods hitherto used is, due to cross reactions they are limited, either to the detection of rheumatoid factors of the class IgM or IgA if human IgG is bound as antigen to the carrier, or that only cross reacting rheumatoid factors can be identified if immunoglobulins of another species, for example of rabbits, are used as antigen instead of human IgG.

It has also been described that the portion of the rheumatoid factor reacting with the Fc part of immunoglobulins is of importance for the diagnosis of rheumatoid arthritis. Still further, it has been reported that the reaction of the rheumatoid factor with the Fc-part of the immunoglobulin takes place only if the respective immunoglobulin has undergone a steric modification in the Fc part by bonding to the antigen or by adsorption onto a carrier or by denaturation (cf. Gell, Coombs, Lachmann, Clinical Aspects of Immunology, 3rd edition, Backwell 1975).

$C1_q$ or $C_3d$ have hitherto been determined by precipitation methods with the use of antibodies specifically directed against $C1_q$ or $C_3d$. It is known that $C1_q$ and $C_3d$ are caused to bind to the Fc part of immunoglobulin when the respective immunoglobulin has undergone a steric modification by being bound to its antigen or to a carrier or by denaturation (for example heat aggregation).

Surprisingly, it has now been found that rheumatoid factors as well as complement factors such as, for example, $C1_q$, bind themselves to the isolated fission product of the immunoglobulin molecule, i.e. the so-called Fc-fragment of IgG, so that the above described disadvantages which occur with the use of immunoglobulins can be overcome.

One of the objects of the invention is, therefore, a process for the determination of Fc-reactants, especially the rheumatoid factor and the $C1_q$ and $C_3d$ factors of the complement, which comprises contacting an aqueous solution containing the substance to be identified with a carrier to which a fission product of an immunoglobulin having an immunologically functioning Fc-portion has been bound by adhesion or chemical reaction, separating the carrier, contacting the Fc-reactant bound to the carrier with an antibody capable of reaction with the Fc-reactant without cross-reacting with the fission product of the immunoglobulin, and determining the amount of antibody.

The determination can be carried out according to methods known from the literature, for example by using a labelled antibody which is directed against the Fc-reactant with determination of the carrier-bound or free labelling agent or by measuring the complement fixation of the antibody reacting with the Fc-reactant.

Suitable labelling agents are enzymes such as peroxidase, fluorescent substances such as fluorescein isothiocyanate (FITC) or radio-active substances such as iodine 131.

The fixation of the complement can be detected by the complement fixation reaction, known to the expert, which is described, for example by J. Humphrey and R. G. White in "Kurzes Lehrbuch der Immunologie" Georg Thieme Verlag, Stuttgart, 1971.

It is another object of the invention to provide a diagnostic agent in which the Fc-fragment of immunoglobulin G is adhesively or covalently bound to a carrier.

In accordance with the process of the invention the diagnostic agent is contacted with the aqueous solution to be tested, preferably a serum sample of the test person, then it is thoroughly washed and finally contacted, for example with a labelled antibody directed against the rheumatoid factor, which antibody does not react with the Fc-fragment.

Suitable antibodies are preferably those directed against the L-chains of Fab- or F(ab)$_2$-fragments of human immunoglobulins and the Fab$_2$ or Fab fission products thereof.

Suitable labelling agents are fluorescent dyestuffs, enzymes or radio-active molecules which are used according to known processes for antibody labelling, for example as described by Wick et al., Immunofluoreszenz, Med. Verlagsgesellschaft Marburg, 1976 or by Nakane et al., J. Histochem. Cytochem. 22, 1048 (1977).

The detection and determination of the bound or unbound labelling agent gives information about the presence and the amount of bound rheumatoid factor, which is a measurement for the amount of rheumatoid factor in the solution.

As mentioned above, the process of the invention can also be used to detect other Fc-reactants, for example Cl$_q$ and C$_3$d components of the complement system. In this case, antibodies directed against Cl$_q$ or C$_3$d are used instead of antibodies against rheumatoid factors.

Fission products of immunoglobulin, in the sense of the invention, which contain the Fc-portion of immunoglobulin or the fragments thereof are, for example, the H-chains of immunoglobulins isolated by the known process of F. Franek, Biochem. Biophys. Res. Comm. 4, 28 (1961); or Fc-fragments or subfragments thereof obtained from immunoglobulins after enzymatic treatment, for example with papain, plasmin or pepsin [cf. H. Bennich, M. W. Turner, Biochem. Biophys. Acta 175, 388 (1969); K. B. M. Reid, Immunology, 20, 649 (1971); R. R. Porter, The Biochemical Journal, 73, 119 (1959); H. Haupt, K. Heide, Klin. Wschr. 47, 270 (1969).

The carrier bound Fc-fragment can be prepared as follows:

A fission product of immunoglobulin with immunologically functioning Fc, for example the Fc-fragment isolated from IgG as described by Haupt and Heide (loc. cit.) or Porter (loc.cit.), is bound to a solid phase by adhesion or covalence.

For adhesive coating the carrier can be treated as described by Deelder et al., Exp. Parasitology, 41, 133 (1977), with the Fc-fragment. To this end, the carrier is treated, for example, with a dilution of 1 g to 1 μg/ml, preferably 20 μg/ml of the Fc-fragment, in aqueous solution (for example phosphate buffered sodium chloride solution ((PBS) of pH 8.4) for 1 minute to 5 days, preferably 24 hours, and then the Fc-fragment in excess is removed by washing with buffer solution (for example PBS, pH 7.2).

For covalent fixation of the Fc-fragment, processes described in the literature and very different carriers can be used [cf. Orth et al., Angew. Chemie, 84, 319 et seq. (1972); Silman et al., Am. Rev. Biochem. 35, 873 et seq. (1966); Howard and Weetall, Immobilized Enzymes, Antigens, Antibodies and Peptides, Marcel Dekker, Inc., New York 1975; Becht et al., J. Immunology, 101, 18 et seq. (1968)].

The determination process is carried out as follows:

The carrier coated with the Fc-fragment either adhesively or covalently is incubated for 10 seconds to 48 hours, preferably for 1 hour, with the test sample, in general blood serum, in a dilution series, preferably 1:1, 1:4, 1:16, 1:32 and so on, at a temperature in the range from 4° to 37° C., preferably at 20° C., and then it is washed to remove serum constituents which have not been bound.

Next, the carrier treated in this manner is contacted with a solution, of a labelled antibody directed against L-chains, Fab- or F(ab)$_2$-fragments of immunoglobulins or against Cl$_q$ or C$_3$d. The appropriate dilution is ascertained in a preliminary test with a solution which does not contain the Fc-reactants looked for. It is the lowest dilution in which the labelled antibody does not react with the carrier coated with the Fc-fragment. The dilution is in the range of from 1:1 to 1:500, preferably 1:100. The incubation is carried out at a temperature of from 4° to 37° C., preferably at 20° C., for 10 seconds to 48 hours, preferably 1 hour. The antibody which has not been bound to the carrier is then removed by washing with a diluent, for example PBS of pH 7.2, and the labelling agent on the carrier or the free labelling agent is determined by a known process.

The carrier-bound fission products of immunoglobulins according to the invention also can be used to carry out a highly sensitive method for the determination of antigen-antibody immuno-complexes, antibody aggregates and antibody fission products. It has been found that, instead of the rheumatoid factor, generally used up to now, antibodies against immunologically modified immunoglobulin can be used for the analysis of antigen-antibody-immuno-complexes, antibody aggregates and antibody fission products. The specificity of the antibodies should be directed against the immunoglobulin which has been modified by fixation to a carrier, to an antigen or by reaction with itself. It can also be directed against fission products of immunoglobulin containing the Fc-part of the said immunoglobulin or fragments of said Fc-part.

It is, therefore, another object of the invention to provide a process for the determination of immunologically modified immunoglobulin, above all of antigen-antibody-complexes, antibody aggregates or antibody fission products in liquids an excess of a Fc-reactant which comprises adding, to a liquid containing the substance to be determined, contacting the mixture with a carrier to which a fission product of the immunoglobulin with immunologically functioning Fc-part has been bound by adhesion or chemical reaction, separating the carrier and determining the free or bound Fc-reactant.

When the Fc-reactant itself is labelled, a conclusion can be drawn from the determination of the labelling agent about the amount of Fc-reactant and, from this, about the immumologically modified immunoglobulin. Although this process is very easy to carry out, it is necessary to prepare the Fc-reactants in a pure state with all the difficulties connected therewith.

It is preferred to use the indirect determination of the Fc-reactant. To this end, an excess amount of the Fc-reactant is added to the liquid containing the immunologically modified immunoglobulin to be determined. The reaction mixture is then contacted with a carrier to which a fission product of the immunoglobulin has been bound by adhesion or chemical reaction. Next, the carrier is separated, washed repeatedly and treated with a labelled antibody directed against antigenic determinants of the Fc-reactant. After washing, the amount of labelling agent bound to the carrier or the free labelling agent is determined.

The process carried out in this manner is distinguished by an especially high sensitivity.

Fc-reactants in the sense of the invention are those compounds which have the ability to bind the so-called Fc-part of an immunologically modified immunoglobulin molecule, preferably the rheumatoid factor (RF), the complement factor ($C1_q$) and antibodies against immunoglobulin which has been immunologically modified in the Fc-part.

The fission product of the immunoglobulin bound to the carrier must still contain the Fc-part or immunologically active fragments thereof.

The antibody labelled with a labelling agent is chosen in such a manner that is does not cross-react immunologically with the fission product of the immunoglobulin on the carrier.

By measuring the amount of labelling agent it is possible to determine the amount of Fc-reactant bound to the carrier or consumed in the analyzed liquid and to infer therefrom the amount of antigen-antibody complexes, antibody aggregates and antibody fission products.

Antibodies against immunoglobulin immunologically modified in the Fc-part are obtained by immunization of animals with an immunologically modified immunoglobulin or with the isolated Fc-part. The immunological modification in the Fc-part can be brought about, for example, by binding the immunoglobulin to a carrier or to an antigen or by reacting it with itself, that is to say by the formation of aggregates.

Suitable carriers, in the sense of the invention, to which the fission products of the immunoglobulin are bound and which may react with Fc-reactants in the form of an agglutination, are especially inorganic and organic shaped structures. Inorganic shaped structures consist, for example, of glass, while the organic shaped structures can be made from homo- or copolymers of vinyl compounds such as olefins, vinyl acetate, vinyl chloride, vinylidene chloride, tetrafluoroethylene, styrene, acrylic acid and methacrylic acid, from polymers of formaldehyde and cyclic acetals, and from polycondensation products such as polyesters, polycarbonates or polyamides. Cross-linked carbohydrates and cross-linked proteins are also suitable. The shaped structures preferably have a spherical or ellipsoidal shape. Planeparallel structures and structures of different shape may also be used, preferably those which are optically-clear, for example microscope slides and test tubes. The shaped structures of organic material may also be of biological origin, erthrocytes of men and animals being preferred. Amorphous substances are further suitable carrier materials.

A preferred object of the invention is an agent for the determination of immunologically modified immunoglobulin in which the Fc-part is bound to an optically clear shaped structure.

The origin of the immunoglobulin to be used for the manufacture of the fission products of the invention depends on the species in which immunologically modified immunoglobulin shall be detected. Optimum results are obtained with a homologous system, i.e. the carrier-bound fission products stem from the same species as the immunologically modified immunoglobulins to be detected. It is also possible, however, to use fission products of other species in the process of the invention provided that they have the ability to undergo an immunologic cross-reaction with the Fc-part of the antibody compounds or antibody fragments to be determined. An example of such a pair of species having the ability of cross-reactions is the combination rabbit/human being.

The complement factor $C1_q$ occurs in nature. It can be isolated, for example, from blood serum and the isolation from the serum of men, rabbits and bovine is described in the literature.

The rheumatoid factor RF is a protein which occurs in the serum of human beings, and more seldom in the serum of other species, suffering from some rheumatoid diseases. RF can be caused to build artifically by immunization with antigen-antibody-complexes or antibody aggregates. Antibody aggregates of this type can be obtained, for example, by heating purified immunoglobulins for several minutes to about 60° C. The rheumatoid factor is also formed by immunization with Fc-containing antibody fragments such as H-chains of immunoglobulins or with Fc-fragments obtained by a treatment of immunoglobulins or of fragments of the Fc-part of immunoglobulins with papain, plasmin or pepsin. After formation of the respective antibody, the fraction containing same is isolated from the serum of the immunized animals by a known method and, if desired, the antibody is concentrated.

Naturally, only the rheumatoid factor having an immunological specificity against the immunologically modified immunoglobulin to be detected in the test liquid as well as against the fission products of immunoglobulins bound to a carrier, is suitable for the invention. A labelled antibody against the Fc-reactant possibly used must not react with the fission products of immunoglobulins bound to a carrier. It is, therefore, necessary that the carrier-bound fission product and the RF stem from different species and/or the antigenic determinants thereof do not undergo immunologic cross-reaction with one another. Hence, for example, an antibody directed against the L-chains of RF may be chosen and for binding to a carrier a fission product of the immunoglobulin free from L-chains.

The following examples illustrate the invention.

EXAMPLE 1

Determination of rheumatoid factors

100 µg of a solution of Fc-fragment of human IgG, prepared by the method of Haupt and Heide [Klin. Wschr. 47, 270 (1969)], in a concentration of 20 µg/ml, in sodium phosphate buffer of pH 8.3 according to Sörensen are introduced into small polystyrene tubes (capacity 400 µg) and the tubes are stored at 20° C. After 18 hours the solution is removed by suction and the tubes are washed three times with phosphate-buffered sodium chloride solution (PBS) containing 0.1% (g/v) of polyoxyethylene sorbitan monolaurate (Tween[R]20) by filling and removal with suction. The emptied and lined tubes are charged with 100 µg each of the rheumatoid factor-containing sample, diluted with PBS in the ratios 1:4, 1:8 and 1:16, and containing 10 mg/ml of bovine serum albumin (BSA) and the tubes are allowed to stand at 20° C. After 2 hours, the solutions are removed with suction and the tubes are washed three times with PBS containing 1 mg/ml of Tween 20 by filling and removing with suction. Next, the tubes are charged with 100 μl each of rabbit-antihuman-L-chain-antibody labelled with peroxydase by the process of Nakane and Kawave, J. Histochem. Cytochem, 22, 1084 (1972) and diluted (1:200, corresponding to 25 ml of antibody protein/ml) with PBS of pH 7.2 containing 50 mg/ml of BSA. After a time of storage of 1 hour at 20° C., the tubes are again washed three times with PBS containing Tween 20 and then 100 μl of a freshly prepared 0.1% o-phenylene-diamine solution in citrate-phosphate buffer (5 ml of 0.1 M citric acid + 5 ml of 0.2 M $Na_2HPO_4$) admixed with 0.1 ml of 1% (v/v) $H_2O_2$ solution are added by a pipette. After a storage time of the tubes of about 30 minutes in the dark, the reaction is stopped by adding 100 μl of 2 N $H_2SO_4$ and the extinction of the reaction solution in the tubes is measured at 490 nm with the aid of a photometer.

In the following Table 1 are indicated the results of 48 sera of patients suffering from rheumatoid diseases compared with the result of a sample free of rheumatoid factor.

TABLE 1

| Detection of RF with carrier bound FC | | |
|---|---|---|
| RF Serum no. (dilution 1:4) | peroxidase reaction valuation E 490 | |
| 157 | 0.253 | + |
| 1 | 0.449 | + |
| 2 | 0.239 | + |
| 8 | 0.289 | + |
| 9 | 0.247 | + |
| 10 | 0.091 | − |
| 11 | 0.255 | + |
| 12 | 0.432 | + |
| 14 | 0.128 | − |
| 15 | 0.251 | + |
| 16 | 0.371 | + |
| 17 | 0.154 | − |
| 18 | 0.322 | + |
| 19 | 0.380 | + |
| 20 | 0.523 | + |
| 21 | 0.281 | + |
| 22 | 0.187 | −/+ |
| 24 | 0.154 | − |
| 25 | 0.137 | − |
| 26 | 0.168 | − |
| 27 | 0.375 | + |
| 28 | 0.435 | + |
| 29 | 0.194 | +/− |
| 31 | 0.153 | − |
| 39 | 0.692 | + |
| 43 | 0.384 | + |
| 45 | 0.219 | + |
| 51 | 0.367 | + |
| 54 | 0.318 | + |
| 56 | 0.460 | + |
| 59 | 0.404 | + |
| 60 | 0.220 | + |
| 62 | 0.364 | + |
| 66 | 0.179 | +/− |
| 68 | 0.241 | + |
| 72 | 0.448 | + |
| 73 | 0.407 | + |
| 75 | 0.256 | + |
| 77 | 0.201 | + |
| 103 | 0.311 | + |
| 105 | 0.209 | + |
| 120 | 0.163 | − |
| 122 | 0.164 | − |
| 123 | 0.335 | + |
| 130 | 0.170 | − |
| 147 | 0.193 | + |

TABLE 1-continued

| Detection of RF with carrier bound FC | | |
|---|---|---|
| RF Serum no. (dilution 1:4) | peroxidase reaction valuation E 490 | |
| 149 | 0.208 | + |
| 155 | 0.323 | + |
| negative control (without rheumatoid factor) | 0.158 | − |

EXAMPLE 2

Determination of the complement factor $C1_q$

Polymethylene methacrylate film with amide groups, introduced by the process of Lynn, Immobilized Enzymes, Antigens, Antibodies and Peptides, Roward and Weetall, Marcel Dekker, Inc. New York, page 32, 1975, is kept for 24 hours at 4° C. in a solution of 10 mg/ml of Fc-fragment of human IgG in PBS of pH 7.2 and then washed three times by immersion in PBS of pH 7.2 containing 10 mg/ml of BSA.

The films coated in this manner are immersed for 2 hours at 20° C. into sera of various patients.

For comparison a PBS solution of pH 7.2 and a second solution containing 50 μg/ml of $C1_q$ and 10 mg/ml of BSA are used.

The films are washed three times by immersion in PBS of pH 7.2 containing 10 mg/ml of BSA and immersed for 2 hours at 20° C. in a solution of rabbit-anti-$C1_q$-antibodies, labelled by FITC, in a concentration of 0.5 mg/ml of PBS of pH 7.2 containing 10 mg/ml of BSA. Next, the films are washed by immersion twice with PBS of pH 7.2 containing 10 mg/ml of BSA and then with distilled water. After drying in air, the foils are glued to an microscope slide by means of an adhesive (Eukitt, free of fluorescence) and the fluorescence is measured in a fluorimeter (Axiomat of Messrs. Zeiss) in comparison with a standard (uranyl glass).

The results are indicated in Table 2. They clearly show the differences in the detection in sera of patients which chronic inflammations and in a positive and negative control solution.

TABLE 2

| FITC fluorescence in comparison with standard Uranyl glass | |
|---|---|
| negative control (no $C1_q$) | 11 |
| positive control ($C1_q$ 50 /μg/ml) | 49.3 + 6.0 |
| sera of patients with chronic inflammations | |
| 1 | 23.9 |
| 2 | 17.2 |
| 3 | 22.6 |
| 4 | 23.4 |
| 5 | 22.1 |

EXAMPLE 3

By cleavage of human immunoglobulin G with papain with subsequent gel chromatographic fractionation of the cleavage produucts by the process of R. R. Porter, The Biochemical Journal 72, (1959), the Fc-fragment is isolated and dissolved in 1% phosphate-buffered sodium chloride solution of pH 8.3.

A film of polymethyl methacrylate (80×250 mm) 50 microns thick is treated for 15 minutes at 90° C. with hydrazine hydrate, rinsed with methanol to which a small amount of acetic acid has been added and then washed with water. Next, the film is introduced into a solution of 1,000 ml of iced water, 500 ml of hydrochloric acid and 120 ml of sodium nitrite solution. After 15 minutes it is washed neutral with iced water and dried in a lyophilization apparatus.

The polymethyl methacrylate film activated in this manner as immersed in a 1% solution of the Fc-fragment in phosphate buffered sodium chloride solution of pH 8.3 and kept in the solution for 48 hours at 4° C. It is then washed three times with phosphate-buffered sodium chloride solution of pH 7.2 and cut into pieces.

For the determination of immunologically modified immunoglobulin in the form of immuno-complexes, a dilution series of the solution to be tested is prepared in phosphate-buffered sodium chloride solution. 40 μl portions of the dilutions of one series are mixed with 40 μl each of human serum having a high content of RF (titer of 1:1,500 in the RF-latex agglutination) and the mixtures are kept for 10 minutes at room temperature. In each mixture a film, covalently coated with Fc-fragments as described above, is immersed and incubated for 2 hours at 20° C. In a control series a 0.9% sodium chloride solution is used instead of the RF-containing serum.

After the films are washed three times in buffered sodium chloride solution of pH 7.2, they are immersed in a 1% solution of rabbit-antihuman-immunoglobulin-L-chain-antibody labelled with fluorescein isothiocyanate (FITC) and kept in the solution for 2 hours at room temperature. The films are then washed twice in phosphate buffered sodium chloride solution of pH 7.2 and once with distilled water.

In an apparatus for the quantitative immunofluorescence determination (Axiomat of Messrs. Carl Zeiss, Oberkochen), the intensity of fluorescence is measured in a predetermined area of the film. The intensity is a measurement for the amount of RF bound to the Fc-fragment, which amount is the smaller the higher the amount of RF bound to immuno-complexes.

The process as described above makes it possible to detect immuno complexes in preparations even in a dilution of 1:8,000.

A comparably high sensitivity can also be reached by using, instead of the rabbit-antihuman-immunoglobulin-L-chain-antibody, an antibody against Fc-fragments of rabbit gamma globulin and/or by using, instead of RF, an antibody against the Fc-fragment obtained by papain cleavage of immunoglobulin.

Instead of RF, human $Cl_q$ and, instead of FITC-labelled rabbit-antihuman-immunogluobulin-L-chain-antibodies, rabbit-anti-$Cl_q$-antibodies labelled with FITC can also be used.

What is claimed is

1. An Fc-sensitive reagent consisting essentially of an immunoglobulin fission product having an immunologically-functioning Fc-portion, said product being bound to a carrier by adhesion or chemical reaction.

2. An Fc-sensitive reagent as in claim 1 wherein said carrier is an optically-clear shaped structure.

3. An Fc-sensitive reagent as in claim 1 wherein said immunoglobulin fission product having an immunologically-functioning Fc-portion is the Fc-fragment of immunoglobulin G.

4. A method for determining an Fc-reactant, which method comprises contacting a liquid containing said Fc-reactant with an Fc-sensitive reagent as in claim 1, separating the carrier from the liquid, reacting the Fc-reactant bound to the carrier with an antibody reacting with said Fc-reactant but not capable of undergoing a cross-reaction with said immunoglobulin fission product, and determining the antibody.

5. A method as in claim 4 wherein the antibody reacting with said Fc-reactant is labelled and the amount of labelling agent bound to the carrier or the amount of free labelling agent is determined.

6. A method as in claim 4 wherein the said Fc-reactant is RF, $Cl_q$, or an antibody against immunoglobulin immunologically-modified in the Fc-part.

7. A method as in claim 4 wherein said Fc-reactant is RF and the antibody used is directed against L-chains or Fab-fragments of immunoglobulins.

8. A method as in claim 4 wherein said Fc-reactant is $Cl_q$ and the antibody used is directed against $Cl_q$.

9. A method as in claim 3 wherein said Fc-reactant is $C_3d$ and the antibody used is directed against $C_3d$.

10. A method for the determination of immunologically-modified immunoglobulin, which method comprises adding an Fc-reactant to a liquid containing the substance to be determined, said Fc-reactant being in excess, contacting the resulting liquid with an Fc-sensitive reactant as in claim 1, separating the carrier from the liquid, and determining the free or bound Fc-reactant.

11. A method as in claim 10 wherein said Fc-reactant is RF, $Cl_q$, or an antibody against immunoglobulin immunologically-modified in the Fc-part.

12. A method as in claim 10 wherein said Fc-reactant is labelled and the labelling agent is determined.

13. A method as in claim 10 wherein said Fc-sensitive reagent, having the Fc-reactant bound thereto, is contacted with a labelled antibody directed against the antigenic determinants of said Fc-reactant and not capable of cross-reacting with the immunoglobulin fission product bound to the carrier, and the free labelling agent or the labelling agent bound to the carrier is then determined.

* * * * *